United States Patent [19]

Johnson et al.

[11] 4,269,064
[45] May 26, 1981

[54] ON-LINE SAMPLER

[76] Inventors: Julius T. Johnson, 348 20th St. S. E., Cedar Rapids, Iowa 52406; Robert R. Johnson, 416 Jacolyn Dr. NW., Cedar Rapids, Iowa 52405

[21] Appl. No.: 44,107

[22] Filed: May 31, 1979

[51] Int. Cl.³ .............................................. G01N 1/12
[52] U.S. Cl. .................................................. 73/422 TC
[58] Field of Search ...................... 73/422 TC, 422 GC

[56] References Cited

U.S. PATENT DOCUMENTS

| 2,906,126 | 9/1959 | Brown | 73/422 TC |
|---|---|---|---|
| 3,200,649 | 8/1965 | Peterson | 73/422 TC |
| 3,218,868 | 11/1965 | Gill | 73/422 TC |
| 3,229,527 | 1/1966 | Johnson | 73/422 TC |
| 3,469,453 | 9/1969 | Nelson | 73/422 TC |
| 3,681,996 | 8/1972 | Crist | 73/422 GC |
| 3,813,945 | 6/1974 | Crumal | 73/423 R |
| 4,009,617 | 3/1977 | Johnson | 73/422 TC |

*Primary Examiner*—Daniel M. Yasich
*Attorney, Agent, or Firm*—Matthew C. Thompson

[57] ABSTRACT

On-line samplers using a piston having its rod reciprocally mounted in a tubular member which reciprocates in a passage, at least the piston and its rod adapted to project out of said passage into the line in which fluid to be sampled is flowing. Upon return of the piston and the tubular member into the passage, a constant volume of sample between the annular faces of the piston and the tubular member is taken into the passage, from which the sample is discharged under positive pressure by moving one of said annular faces into substantially face-to-face contact with the other annular face.

14 Claims, 4 Drawing Figures

ON-LINE SAMPLER

INTRODUCTION

This invention in general pertains to samplers adapted to withdraw at predetermined intervals constant volume samples of fluids flowing through a pipe, conduit, vessel or the like, and are herein referred to as on-line samplers in the sense that they are mounted on such conduits, pipes and the like. The samples are useful in sampling of liquid of all types but are particularly useful in the sampling of liquids whose composition varies frequently or from time to time. One example is milk, in which the butterfat content varies even in one batch. Another example is sewerage.

Briefly, the samplers of the invention entrap a liquid sample in a chamber which is a collapsible annular space formed in a passageway about a piston rod and between opposed, annular faces of a piston and a tubular member through which the piston rod passes. The piston is first fully projected into the pipe, conduit, etc. from which the sample is to be withdrawn, thereby allowing fluid flowing through the pipe, etc. to enter the zone around the rod and between the annular faces. The tubular member and the piston are drawn into the passageway—the annular chamber being formed when the piston enters the passageway, thereby withdrawing a liquid sample of predetermined volume. The passageway has a discharge port through which the sample is discharged for collection.

Sample discharge is achieved by moving the piston toward the tubular member (or vice versa) after the piston is in the passageway until the annular faces are substantially or actually in face-to-face contact. This movement collapses the annular chamber and forces the liquid sample through the discharge port.

The reciprocal motion imparted to the tubular member and the piston rod may be accomplished by mechanical drives, electro-mechanical drives, servo drives, solenoids, pneumatic or hydraulic drives, etc. The illustrated embodiments utilize a pneumatic unit. In all instances, the drives are connected to the piston rod and the tubular member so that a positive motion is applied to move the piston toward the tubular member or the tubular member toward the piston when they are in the sample discharge position—whereby the sample is ejected through the discharge port under positive pressure.

PRIOR ART

There are several types of known, on-line samplers. J. T. Johnson, U.S. Pat. Nos. 3,229,527 and 4,009,617 disclose on-line samplers having a sample-intake chamber and a separate sample-discharge chamber—each with respective valves—and a pneumatically operated diaphragm which, when moved by air pressure applied on one side of the diaphragm, closes a check valve at the fluid entry port of the first chamber and exerts pressure on sample fluid within the passages of the sampler. This pressure opens a spring-loaded pop valve and allows a given volume of sample fluid to enter a discharge chamber from which the sample is collected. Upon release of the air pressure, the liquid pressure in the line opens the check valve in the first chamber and the chamber fills with the next volume of sampled fluid.

S. S. Brown, U.S. Pat. No. 2,906,126 describes a sampler with two coaxial tubes with normally aligned ports through which fluid enters the sampler. The inner tube is moved axially to disalign the ports to isolate the sample then in the tubes and allow the sample to flow out of the lowest ports for collection.

STATEMENT OF THE INVENTION

The on-line samplers of this invention comprise a body having a passage therethrough. One end of the passage opens into the pipe or conduit or other member through or past which a fluid is flowing. A tubular member is slidably mounted in the passage while a piston rod is slidably mounted in the tubular member. The piston and tubular member reciprocate between a first, sample-taking position in which the piston completely projects from the passage and a second, sample discharge position within the passage. In the latter position, motion is imparted to one of these two parts to cause the sample to be discharged.

The opposed, annular faces of the piston and the tubular member are spaced apart by a predetermined distance while taking a sample, i.e., when the piston projects from the passage. This spacing is maintained while the tubular member and piston are simultaneously drawn into the passage to a sample discharge position in which the piston is within the passage. The liquid sample is entrapped in the annular space formed between the opposed annular faces of the piston and the tubular member, the piston rod, and the passage wall. The tubular member and piston retract in the passage to a sample discharge position. A port for discharge of the sample communicates with the annular space and the sample therein when they are in the sample discharge position.

At this point, either the piston is moved toward the tubular member or the tubular member is moved toward the piston until their opposed annular faces actually or substantially are in face-to-face contact. This action pumps essentially all of the liquid sample through the port for collection in a suitable receptacle, e.g., a metal or glass vessel, a plastic bag, or the like.

In the illustrated embodiments, the piston and tubular members are reciprocated as aforedescribed by a pneumatic power drive. The latter has a pneumatic cylinder with pressurized air inlet and vent ports. It has a hollow piston connected to the tubular member, and is reciprocated in the pneumatic cylinder by air pressure applied to either side thereof.

A disc piston serves as the pneumatic drive for the piston rod. The disc piston reciprocates in a cylindrical chamber within the hollow piston. In the sample intake stroke, it has essentially no relative movement with reference to the hollow piston until the latter stops with the annular sampling chamber aligned with the discharge port. When the hollow piston stops, the pneumatic pressure applied to the disc piston causes it to move within the cylindrical chamber and thereby move the piston toward the tubular member, causing the annular smapling chamber to collapse substantially completely. The disc piston moves until the annular faces of the sampling chamber are in actual or substantial face-to-face contact.

The return stroke of the tubular member and the piston involves simultaneous movement thereof toward the open end of the passage in which the sampling piston again resumes its spaced relationship to the tubular member. Such spaced relationship may be accomplished before, during or after the tubular member and sampling piston travel to the sampling position, i.e., the position in which the sampling piston extends completely out of the open end of the passage into the pipe, conduit, etc., from which the next liquid sample is to be taken. In the illustrated embodiments, pressurized air is admitted into the hollow piston of the pneumatic chamber. This drives the disc piston toward the open end of the passage—thereby separating the opposed, annular faces of tubular member and sampling piston—until the disc piston contacts the hollow piston. Then both pistons move together until the hollow piston is arrested by abutting contact with stop means in the pneumatic cylinder.

The rest position for the sampling piston and tubular member depends on the timing of the pneumatic controls. Such rest position may be one with these members wholly within the passage, e.g., with the annular faces in actual or substantial contact, or one in which the sampling piston and its position rod are projected into the pipe, conduit, etc. In the latter position, the piston and piston rod are continuously washed by the flowing liquid until they are retracted into the passage for sample taking purposes.

THE ILLUSTRATED EMBODIMENTS

Preferred embodiments of the invention are illustrated in the drawings, wherein.

Figure 1:
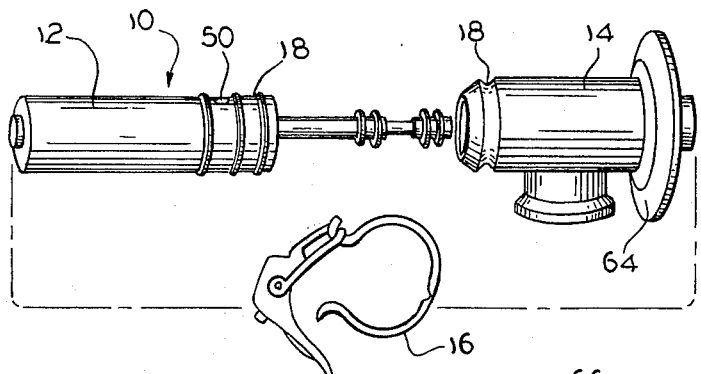
FIG. 1 is an exploded, perspective view of a first embodiment on an on-line sampler and a clamp for securing same on a pipe, conduit, etc.
Figure 2:
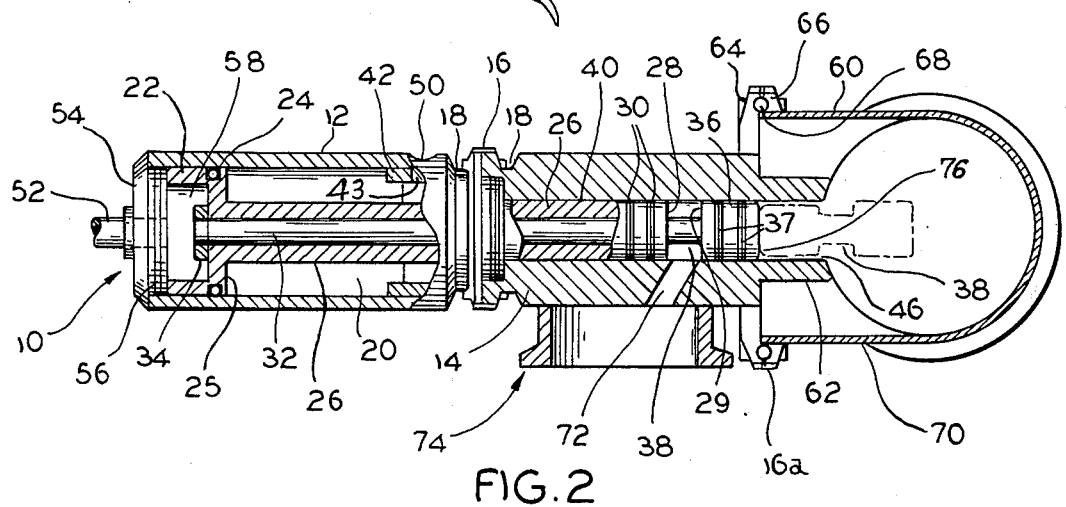
FIG. 2 is a diametric section of said embodiment mounted on a T-coupling of the pipe, conduit, etc.

Referring to FIG. 1, the on-line sampler 10 embodies a pneumatic drive cylinder 12, a sample intake cylinder forming a housing 14 and a ring clamp 16 used in conjunction with annular grooves 18 to clamp the two members together in the axial alignment shown in FIG. 2. The pneumatic cylinder 12 has a piston chamber 20 in which a hollow, cylindrical piston 22 is reciprocally driven by pneumatic pressure. The tubular piston rod on member 26 for the hollow piston extends coaxially through the pneumatic chamber 20 and into an axial, cylindrical passage 40 which extends through the cylinder 14. An O-ring 24 provides a substantially air-tight, sliding seal between the external cylindrical surface of the hollow piston 22 and the piston chamber 20. The hollow piston is composed of a cylinder wall 22 and one end wall 25.

A piston rod 32 for the sampling piston 36 and having a stop 34, e.g., a washer or flange on one end thereof, is slidably mounted in the axial, cylindrical passage of the tubular rod 26. The annular face 28 on the opposite end of the tubular rod provides one face of an annular, collapsible sampling chamber 38, hereinafter described. O-rings 30 seal off the small annular clearance between the tubular rod 26 and the cylindrical passage 40.

The sampling piston 36 is mounted on the piston rod 32. When the piston 36, which also has O-ring seals 37, is fully extended relative to the tubular member 26, the opposed annular faces 28 and 29 on the tubular rod and piston, the piston rod 32 and the cylindrical wall of the axial passage 40 form an annular sampling chamber 38 of predetermined, constant volume, i.e., the hollow cylindrical space about the rod 32 between the faces 28 and 29.

To extend the sampling piston 36 to its projected, sample-taking position shown in phantom lines in FIG. 2, pressurized air is admitted through line 52, thereby moving the piston 22, its tubular rod 26, the sampling piston 36 and its piston rod 32 toward the open end 46 of the cylindrical passage 40. Air in the pneumatic cylinder 20 ahead of the piston 22 is vented through port 50. A ring 42 with a passage 43 communicating with port 50 at the opposite end of the pneumatic cylinder arrests the piston 22, in which position the piston 36 and its rod 32 have emerged from the open end 46 of the passage 40, i.e., in the position shown in phantom lines.

During the aforesaid movements, the annular face 28 of the tubular rod and the opposed annular face 29 of the piston assume the spacing therebetween shown in FIG. 2. Pressurized air admitted by line 52 exerts pressure against the end of the piston rod 32 and its washer or flange 34 and drives the rod 32 within the tubular rod 26 until the washer or flange is stopped by the end wall 25 of the hollow piston.

For sample intake, pressurized air is admitted through port 50. Air is vented from the pneumatic cylinder via line 52. The hollow piston, its tubular rod, the piston rod 32, and its sampling piston move as a unit with the annular faces 28, 29 still spaced apart to the sample-discharge position shown in FIG. 2. Such position is reached when the hollow piston 22 strikes the end wall 54.

The embodiment of FIG. 2 is used to sample fluids under pressure, which line pressure is used to collapse the sampling chamber. Fluid pressure exerted against face 76 of the piston 36 drives the piston toward the tubular rod 26 until the annular faces 28 and 29 are in face-to-face contact. This movement of the piston imparts a positive, pumping pressure on the sampled fluid and causes it to flow into the discharge port 72. The pumping action and the collapse of the sampling chamber to substantially zero volume assures collection of a series of samples, each having a predetermined, constant volume, during the overall sampling process. The collected samples together provide an average for the fluids of varying composition, e.g., milk, which flow through the pipe, conduit, etc.

Figure 3:
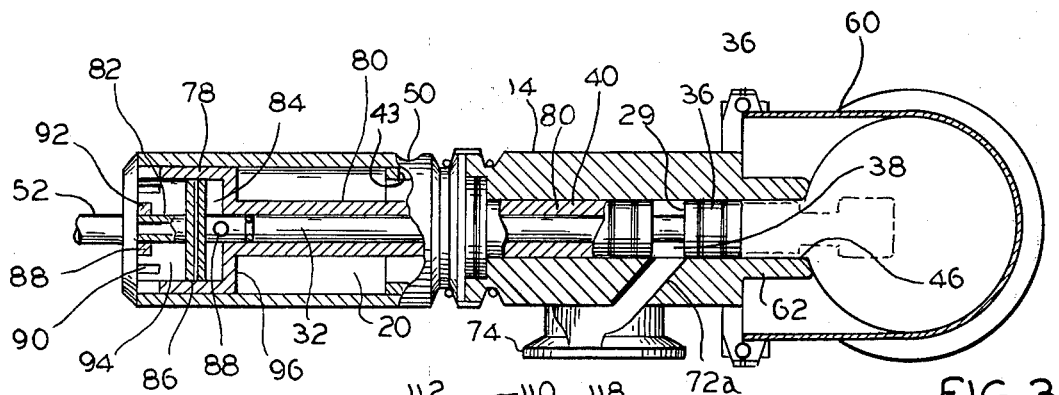
FIG. 3 is a section similar to FIG. 2 with a second embodiment of the pneumatic drive.

One technique for mounting the sampler on a pipe or other conduit means is shown in FIG. 2. The sampler is mounted on a T-coupling 60 in the conduit means to be sampled. A flange 64 near the end of the cylinder 14 is laid against a corresponding flange 66 on the T-coupling. The two flanges are held together by a ring clamp 16a, which is like ring clamp 16. Additional details of the connection on a T-coupling may be found in J. T. Johnson, U.S. Pat. No. 4,009,617, wherein a sampler assembly is shown in FIGS. 2 and 3 thereof mounted by means of a ring clamp 15 on a T-coupling 11 on the conduit means 10 containing the fluid to be sampled. A ring gasket 68 provides a fluid tight seal. As is seen in FIG. 2, the cylinder 14 has a tubular nose portion 62 which extends out of the end 46 of the passage 40 into or adjacent the stream of fluid flowing through the T-coupling. This is done so that the extended sampling piston and its rod are exposed to fluid flowing through the line and avoids possible taking of non-representative samples from fluid in the "dead-flow" zone of the T-leg 70 on which the sampler is mounted.

The samples may be collected in any suitable receiving device. In FIGS. 1 and 2, the discharge port 72 opens into a flanged coupling 74, on which may be mounted by a ring clamp or the like a collection vessel (not shown) or plastic collection bag and its mounting adapter (not shown). For details of the latter, attention is directed to the aforesaid U.S. Pat. No. 4,009,617.

The embodiment of FIG. 3, except for the details of the pistons in the pneumatic cylinder, is similar to that of FIGS. 1 and 2. Where applicable, like numerals designate like parts.

The pneumatic drive of FIG. 3 provides a drive system which causes the sampling chamber to collapse by pneumatic pressure, rather than relying on fluid pressure in the line being sampled. Here, the hollow piston 78 and its tubular piston rod 80 move toward the sampling piston 36 during collapse of the sampling chamber. When pressurized air is supplied to line 52, it initially flows into a tubular extension 82 of the piston rod 32 of disc piston 86. The extension 82 initially remains seated in the tubular socket 92 which projects through the end wall of the pneumatic cylinder, whereby only the space 84 between the disc piston 86 and the end wall of the hollow piston 78 initially receives pressurized air via the port 88. Thus the pressurized air holds the extension 82 in the socket 84 while the hollow piston and its tubular piston rod 80 move toward the stationary sampling piston 36, thereby collapsing the sampling chamber and discharging fluid sample through the discharge port 72a. The port 72a opens into the sampling chamber adjacent the annular face 29 of the piston in this embodiment, whereas the port 72 in the embodiment of FIG. 2 opens into the sampling chamber adjacent the annular face 28 of the tubular piston. When faces 28 and 29 come into substantial face-to-face contact, longitudinal grooves 90 in the inside face of the cylindrical wall of the hollow piston 78 will have just passed the disc piston 86. This allows pressurized air in the space 84 to flow past the disc piston 86 into the space 94. When space 94 becomes pressurized, the disc piston begins to travel toward the end wall 96 of the hollow piston. Tubular extension 82 thereby becomes unseated from the socket 92. The disc piston moves inside hollow piston until stopped by the end wall 96, thereby moving the sampling piston 36 away from the tubular piston rod 80 and reforming the sampling chamber 38. When the disc piston contacts the end wall 96, both the sampling piston and the tubular piston rod 80 move simultaneously toward the open end 46 of passage 40 until they reach the projected position shown in phantom lines.

When sample is to be taken into the passage 40, pressurized air is admitted through port 50 and is vented through the line 52. This drives the hollow piston 78, which in turn pushes the disc piston 86, rearwardly until the hollow piston is arrested by the end wall of the chamber 20. This is the position shown in FIG. 3. The sample is discharged through port 72a as previously described. It is to be noted that the ports 72 and 72a in FIGS. 2 and 3 are flush with or slightly overlap the face 28 of the tubular member 80 and the face 29 of the piston 36, respectively, during sample discharge. These are the faces of the members which remain stationary during sample discharge and thus the ports 72 and 72a remain open during the entire sample discharge stroke, whereby all of the sample is discharged in each stroke.

Figure 4:
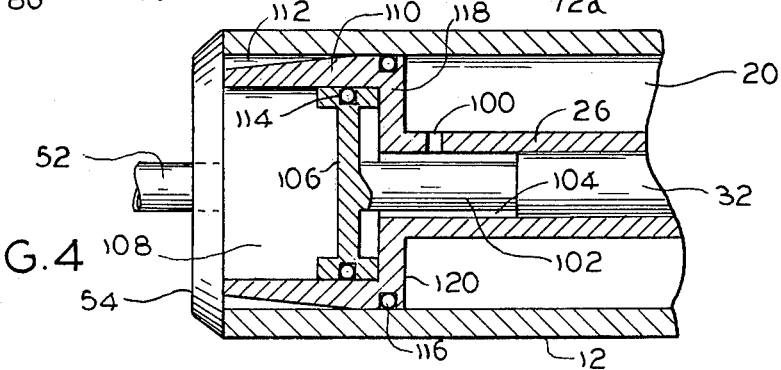
FIG. 4 is a fragmentary, diametric section of the pneumatic cylinder of still another embodiment of the pneumatic drive.

In FIG. 4, only the rear segment of the pneumatic chamber is shown. This embodiment may be used in the sampler shown in FIG. 2 to attain positive pressure discharge from the pneumatic drive instead of relying on line pressure to collapse the sampling chamber. Here the tubular member 26 has a small port 100 in its rearward portion. The rear portion of the piston rod 32 has stepped shank 102 of smaller diameter than that of the rod, thereby providing an annular space 104 for flow of pressured air.

The shank 102 is connected to the flanged disc piston 106 which reciprocates within the cylindrical chamber 108 inside the hollow, outer piston 110. A segment 112 of the outer wall of piston 110 is tapered. O-rings 114 and 116 seal against air pressure loss along the outer faces of the two pistons.

The pistons 106 and 110 are in the positions shown in FIG. 4 when the tubular member and sample piston are in the full line position shown in FIG. 2. Pressurized air is admitted to the chamber 20 and flows through port 100 and space 102 to drive the disc piston 106 rearwardly until it is stopped by face 28. This discharges the sample by moving the sampling piston 36 (FIG. 2) toward the end of the tubular member 26.

To extend the sampling piston and tubular member to the phantom line position shown in FIG. 2, pressurized air is admitted through the conduit 52 while the chamber 20 is vented via port 50 (FIG. 2). This drives disc piston 106 forwardly until its flange strikes the end wall 118 of the hollow piston. Thereafter, both pistons move forwardly until arrested by the stop ring 42 (FIG. 2) in the pneumatic chamber, whereby the sampling piston and the segment 38 of the piston rod 32 are positioned within the fluid flowing through the pipe, conduit, etc.

The return stroke is accomplished by admitting pressurized air into chamber 20 and venting via conduit 52. Because of the relatively large area of the face 120 of the hollow piston and the small size of port 100, piston 106 does not move initially within the chamber 108, whereby the maximum spacing between the face 29 of the sampling piston 36 and the face 28 of the tubular member 26 is maintained while the sampling piston reenters the passage 40. When the piston 110 strikes the end wall 54, the sample is discharged under positive pressure as described above.

The foregoing embodiments constitute preferred forms of the invention. It is to be noted, however, that the invention as herein claimed covers many other forms and the invention as claimed is not limited to the illustrated embodiments.

What is claimed is:

1. Apparatus adapted to be mounted on a fluid conduit for sampling a fluid flowing through said conduit, said sampling apparatus comprising:
   a housing having an axial passage with an open end adapted to be in communication with the fluid flowing through said conduit;
   a sample-taking means including a collapsible, annular sampling chamber of predetermined volume;
   means for reciprocating said sample-taking means within said axial passage between a first sample-taking position wherein said sample-taking means projects from said open end of said axial passage and is exposed to the fluid flowing through said conduit and a second sample-discharge position wherein said sample-taking means is withdrawn within said axial passage;
   said annular sampling chamber of predetermined volume being defined by the inner wall of said axial passage when said sample-taking means is reciprocated to its second sample-discharge position, by the annular face of the end of a tubular member reciprocably mounted in said axial passage, by an opposed annular face of a sampling piston mounted on a piston rod reciprocably mounted in said tubular member and extending therethrough, and by said piston rod extending between said sampling piston annular face and the opposed annular face of the end of said tubular member;

drive means operatively connected to said sample-taking means to reciprocate one of said sampling piston or said tubular member away from and towards the other between extreme positions whereby, when said sample-taking means is reciprocated to its second sample-discharge position, said sampling chamber of predetermined volume will be collapsed to a position where said sampling piston annular face and the opposed annular face of the end of said tubular member are substantially in face-to-face contact, and whereby when said sample-taking means is reciprocated to its first sample-taking position said sampling chamber will be expanded back to its predetermined volume; and a fluid discharge means in said housing communicating with said sampling chamber when said sample-taking means is reciprocated to its second sample-discharge position whereby the predetermined volume of sampled fluid will be discharged into said fluid discharge means upon the collapse of said sampling chamber.

2. Apparatus as claimed in claim 1 wherein said drive means embodies said reciprocating means whereby said tubular member and said sampling piston may be reciprocated within said axial passage to said first sample-taking position wherein the sampling piston and said piston rod extend from said axial passage into the fluid flowing through said conduit with the annular face of said sampling piston at a predetermined spacing from the opposed annular face of the side of said tubular member and whereby said tubular member and said sampling piston may be reciprocally withdrawn back at said predetermined spacing into said passage to said second sample-discharge position.

3. Apparatus as claimed in claim 2 wherein said drive means includes means to permit said sampling piston to move to its collapsed position where its annular face is in substantially face-to-face contact with the opposed annular face of the end of said tubular member under the line pressure of said fluid flowing through said conduit acting against the outer face of said sampling piston when said sample-taking means is reciprocated to its second sample-discharge position.

4. Apparatus as claimed in claim 2 wherein said drive means includes a power-operated means to move said tubular member toward said sampling piston in said second sample-discharge position until said sampling piston and tubular member end annular faces are substantially in face-to-face contact.

5. Apparatus as claimed in claim 2 wherein said drive means includes a power-operated means to move said sampling piston toward said tubular member in said second sample-discharge position until said sampling piston and tubular member end annular faces are substantially in face-to-face contact.

6. Apparatus as claimed in claim 2 wherein said drive means is a pneumatic drive means.

7. Apparatus as claimed in claim 6 wherein said pneumatic drive means embodies a pneumatic chamber with a hollow piston connected to said tubular member and reciprocally driven in said chamber by pneumatic pressure, and a further piston reciprocally movable within said hollow piston and connected to said piston rod.

8. Apparatus as claimed in claim 7, and means for reciprocating said further piston within said hollow piston by pneumatic pressure in the direction wherein said sampling chamber is substantially completely collapsed by the pneumatic pressure exerted on said further piston.

9. Apparatus for sampling a fluid flowing through fluid conduit means comprising a sampler adapted to be mounted on said conduit means; said sampler embodying a housing having an axial passage with an open end portion adapted to be in communication with fluid flowing through said conduit means; sample-taking means with opposed annular faces normally spaced apart at a constant, predetermined spacing, said spaced, annular faces forming, in conjunction with the wall of said axial passage, a collapsible, annular sampling chamber of constant, predetermined volume; means to reciprocate said sample-taking means within said passage between a first position wherein the sampling taking means, with its opposed, annular faces spaced apart at said constant, predetermined spacing, projects at said open end portion of said passage into the fluid in said conduit means and a second position wherein said sample-taking means, with its opposed, annular faces spaced apart at said constant, predetermined spacing, is within said passage and said annular sampling chamber of constant, predetermined volume is thereby formed; drive means operatively connected with said sample-taking means to bring said opposed, annular faces into substantially face-to-face contact and thereby substantially completely collapse said sampling chamber when it is in sample discharge position within said passage; and fluid discharge means in said housing for discharge of the sampled volume of fluid from said passage under positive pressure upon the collapse of said sampling chamber, said annular sampling chamber being defined by said axial passage, by the annular face of the end of a tubular member reciprocably mounted in said axial passage, by an opposed annular face of a piston mounted on a piston rod reciprocably mounted in said tubular member and extending therethrough, and by said piston rod, and said drive means being operable to move one of said sampling piston and said tubular member toward and away from the other between extreme positions providing said substantially face-to-face contact and said constant, predetermined spacing.

10. Apparatus as claimed in claim 9, wherein said drive embodies means to move said tubular member and said sampling piston to a position wherein the piston and its rod extend from said axial passage with the annular face of said sampling piston at said predetermined spacing from the annular face of said tubular member and also means to return said sampling piston while maintaining said predetermined spacing back into said passage to the sample discharge position.

11. Apparatus as claimed in claim 9, wherein said drive means embodies means to allow said sampling piston to move into said substantially face-to-face contact in said sample discharge position under line pressure of the fluid in said conduit means against the outer face of said piston to attain substantially complete collapse of the sampling chamber and thereby discharge the sampled volume of fluid within said sampling chamber under positive pressure.

12. Apparatus as claimed in claim 9, wherein said drive means embodies power-operated means to move said tubular member toward said piston in said sample discharge position until said annular faces are substantially in face-to-face contact to attain substantially complete collapse of the sampling chamber and thereby discharge the sampled volume of fluid under positive pressure.

13. Apparatus as claimed in claim 9, wherein said drive means embodies power-operated means to move said piston toward said tubular member in said sample discharge position until said annular faces are substantially in face-to-face contact to attain substantially complete collapse of the sampling chamber and thereby discharge the sampled volume of fluid under positive pressure.

14. Apparatus as claimed in claim 9, wherein said drive means is a pneumatic drive means.

* * * * *